(12) United States Patent
Sparbier et al.

(10) Patent No.: US 11,307,122 B2
(45) Date of Patent: Apr. 19, 2022

(54) PREPARATION OF BIOLOGICAL CELLS ON MASS SPECTROMETRIC SAMPLE SUPPORTS FOR DESORBING IONIZATION

(71) Applicant: Bruker Daltonik GmbH, Bremen (DE)

(72) Inventors: Katrin Sparbier, Bremen (DE); Beatrix Wegemann, Bremen (DE)

(*) Notice: Subject to any disclaimer, the term of this patent is extended or adjusted under 35 U.S.C. 154(b) by 395 days.

(21) Appl. No.: 15/968,428

(22) Filed: May 1, 2018

(65) Prior Publication Data

US 2018/0328822 A1    Nov. 15, 2018

(30) Foreign Application Priority Data

May 15, 2017 (DE) .......................... 102017110476.3

(51) Int. Cl.
| | |
|---|---|
| G01N 1/40 | (2006.01) |
| G01N 1/28 | (2006.01) |
| C12Q 1/04 | (2006.01) |
| C12Q 1/18 | (2006.01) |
| G01N 33/68 | (2006.01) |

(52) U.S. Cl.
CPC ........... *G01N 1/4044* (2013.01); *C12Q 1/045* (2013.01); *C12Q 1/18* (2013.01); *G01N 1/28* (2013.01); *G01N 33/6851* (2013.01); *G01N 1/4055* (2013.01)

(58) Field of Classification Search
CPC .... G01N 1/4044; G01N 1/28; G01N 33/6851; G01N 1/4055; G01N 27/62; G01N 1/40; G01N 1/286; C12Q 1/045; C12Q 1/18
See application file for complete search history.

(56) References Cited

U.S. PATENT DOCUMENTS

| | | | |
|---|---|---|---|
| 7,485,855 B2* | 2/2009 | Sundaram ................ | G01N 1/34 250/281 |
| 7,888,637 B2 | 2/2011 | Finch et al. | |
| 99,557,473 | 5/2018 | Biomérieux | |
| 10,011,860 B2 | 7/2018 | Lange et al. | |
| 2002/0045270 A1 | 4/2002 | Schurenberg et al. | |
| 2005/0087685 A1 | 4/2005 | Bouvier et al. | |
| 2006/0016984 A1* | 1/2006 | Finch ....................... | G01N 1/40 250/288 |
| 2007/0224688 A1* | 9/2007 | Feuer ...................... | B82Y 30/00 436/86 |
| 2008/0009029 A1* | 1/2008 | Govorun ............ | G01N 33/6851 435/32 |
| 2008/0056945 A1 | 3/2008 | Hattori | |
| 2012/0107864 A1* | 5/2012 | Sparbier ................. | C12Q 1/04 435/34 |
| 2013/0009712 A1 | 1/2013 | Braganca et al. | |
| 2013/0337502 A1 | 12/2013 | Bo meyer et al. | |
| 2015/0136972 A1 | 5/2015 | Lasch et al. | |
| 2016/0298164 A1 | 10/2016 | Sparbier et al. | |
| 2016/0333388 A1 | 11/2016 | Kostrzewa et al. | |
| 2016/0379811 A1 | 12/2016 | Lam et al. | |

FOREIGN PATENT DOCUMENTS

| | | |
|---|---|---|
| DE | 10043042 A1 | 3/2002 |
| DE | 102004019043 A1 | 1/2006 |
| DE | 102010019869 A1 | 11/2011 |
| DE | 102012011647 A1 | 12/2013 |
| DE | 102012011648 A1 | 12/2013 |
| DE | 102014000646 A1 | 7/2015 |
| EP | 2806275 A1 | 11/2014 |
| EP | 3081652 A1 | 10/2016 |
| JP | 2005513479 A | 5/2005 |
| JP | 2006517671 A | 7/2006 |
| JP | 2016518604 A | 6/2016 |
| KR | 1020170042646 | 4/2017 |
| WO | 2003054543 A2 | 7/2003 |
| WO | 2005123242 A1 | 12/2005 |
| WO | 201628684 A1 | 2/2016 |
| WO | 2016191646 A2 | 12/2016 |

OTHER PUBLICATIONS

Matsuda, Naoto, et al. "Evaluation of a simple protein extraction method for species identification of clinically relevant staphylococci by matrix-assisted laser desorption ionization-time of flight mass spectrometry." Journal of clinical microbiology 50.12 (2012): 3862-3866. (Year: 2012).*

Penny, Christian, et al. "A designed experiments approach to optimizing MALDI-TOF MS spectrum processing parameters enhances detection of antibiotic resistance in Campylobacter jejuni." Frontiers in microbiology 7 (2016): 818. (Year: 2016).*

Agnés Ferroni et al.: "Real time identification of bacteria and yeast in positive blood 1 culture broths by MALDI-TOF-Mass Spectrometry", Journal of Clinical Microbio., p. 21, Mar. 17, 2010.

Bruker: MALDI Biotyper Consumables Added Convenience Enhances Assay Productivity, Aug. 2015.

E.A. Idelevich et al.: "Direct blood culturing on solid medium outperforms an automated continuously monitored broth-based blood culture system in terms of time to identification and susceptibility testing", New Microbes and New Infections, pp. 19-24, Dec. 23, 2015.

(Continued)

*Primary Examiner* — Robert J Yamasaki
(74) *Attorney, Agent, or Firm* — Benoit & Côté Inc.

(57) ABSTRACT

The invention relates to the preparation of biological cells for the mass spectrometric analysis of cellular properties such as taxonomic classification, antibiotic resistances, response to drugs or other active substances, and others. The cells can be prokaryotic or eukaryotic microorganisms which have particularly been cultivated directly on a mass spectrometric sample support, or eukaryotic cells from tissues or cell cultures. The invention proposes that the cells are not disrupted by adding matrix solution for a subsequent ionization by matrix-assisted laser desorption (MALDI), but that they are disrupted in a separate treatment step using acids and/or solvents on the sample support itself. Surprisingly, the cell proteins released then adhere to the sample support so that they can be carefully washed with buffer solution to remove salts and other soluble impurities which can stem from earlier treatment steps, for example from nutrient solution.

21 Claims, 3 Drawing Sheets

(56) References Cited

OTHER PUBLICATIONS

Franco Basile: "Rapid Sample Preparation for Microorganism Analysis by Mass Spectrometry" ACS Symposium Series, American Chemical Society/Oxford University Press, Jun. 6, 2011.
Lingjun Li et al., "In Situ Sequencing of Peptides from Biological Tissues and Single Cells Using MALDI-PSD/CID Analysis", Analytical Chemistry, vol. 71, No. 24, Dec. 15, 1999.

* cited by examiner

A: Sensitive strain in Mueller-Hinton medium without antibiotic
B: Sensitive strain in Mueller-Hinton medium with antibiotic
C: Meropenem-resistant strain in Mueller-Hinton medium without antibiotic
D: Meropenem-resistant strain in Mueller-Hinton medium with antibiotic

PREPARATION OF BIOLOGICAL CELLS ON MASS SPECTROMETRIC SAMPLE SUPPORTS FOR DESORBING IONIZATION

BACKGROUND OF THE INVENTION

Field of the Invention

The invention relates to the preparation of proteins from biological cells on mass spectrometric sample supports for the mass spectrometric analysis of cellular properties such as taxonomic classification (identity), antibiotic resistances, response to drugs or other active substances, and others. The cells can be prokaryotic or eukaryotic microorganisms or eukaryotic cells from tissues; they can particularly have been cultivated on sample support plates in culture media, to enable conclusions to be drawn about specific cellular properties from their growth under certain influences, for instance in the presence of specific substances.

Description of the Related Art

The patent application PCT/DE2016/100561 (K. Becker and E. Idelevich: "Aufbereitung lebendiger, mikrobieller Proben und Mikroorganismen für anschließende massenspektrometrische Messung und Auswertung" ("Preparation of Living, Microbial Samples and Microorganisms for Subsequent Mass Spectrometric Measurement and Evaluation")) describes in detail how microbes on mass spectrometric sample support plates can be incubated in nutrient solutions, for example with and without the addition of antibiotics, in order to determine whether a resistance exists or not by observing further growth. This document and all its content shall be incorporated herein by reference.

The method described in this document represents a novel method for a very fast and simple MS-based analysis of particular properties of biological cells; for example regarding the response of cells to antibiotics or drugs or in respect of the further characterization of biological cells. The disclosure relates in particular to the method of sample processing and sample preparation and also to data evaluation algorithms.

A preferred aspect of the document cited relates to a method to prepare living, microbial samples for a subsequent mass spectrometric measurement, which comprises the following steps: (a) Provide a flat sample support containing several application sites for samples (so-called "spots"); (b) deposit at least one living, microbial sample in a culture medium droplet on at least one of the sample spots; (c) place the sample support in an incubation chamber with a defined atmosphere for a predetermined period of time in order to allow the microorganisms to grow and propagate; (d) remove residual liquid from the culture medium droplet after the predetermined period of time in order to expose a deposit of microorganisms on the sample spot; (e) prepare the sample spot for a desorbing ionization; (f) transfer the sample support into a desorption ion source of a mass spectrometer, generate ions from the prepared sample spot and acquire at least one corresponding mass spectrum; and (g) compare the mass spectrum acquired with a set of reference data to determine at least one property of the microbial sample.

This method can be used, for example, to determine the growth of the microbial cells in the presence of different types of antibiotics: further growth reveals whether the microbial cells are resistant or susceptible to the antibiotic used.

The method occasionally encounters difficulties. The separation of the microbes from the residual liquid with the methods stated, such as drawing off with a pipette or a sheet of blotting paper, may not succeed when the microbes swim on the surface of the liquid, as is the case with salmonella and other flagellates, for example, because there is then a high risk that the microbes are drawn off also. Drying the nutrient solution in order to bind the cells to the sample support surface and subsequently prepare them leaves behind salts and other constituents from the nutrient solution which have a detrimental effect on the ionization by matrix-assisted laser desorption and significantly reduces the sensitivity for many proteins. It is also frequently the case that the dried microbe samples cannot be washed, since the microbes of many species do not adhere firmly enough to the surface of the sample support after the nutrient solution has dried.

Very generally, biological cells must be disrupted to measure their constituents, particularly their proteins, in order to release the proteins for a subsequent ionization. "Disruption" in this context means the destruction of the cell walls and the breaking up of protein complexes inside the cell so that the proteins can migrate out of the cells.

Two methods are recommended for this disruption: (1) An "external" disruption by centrifugation of washed microbes with the aid of acids in a special vessel, further centrifugation and transfer of the supernatant with the proteins from the cells onto the mass spectrometric sample support, and (2) disruption of the cells applied to the sample support by adding a solution of the matrix substance, i.e. an organic acid in an organic solvent, which allows most microbes to be disrupted. The matrix solution simultaneously prepares the sample for the subsequent ionization by matrix-assisted laser desorption (MALDI). In methods for the identification of microbes, the external disruption provides a higher percentage of unequivocal identifications, but takes significantly longer because of the multiple centrifuging, and is more work-intensive.

In the paper "Evaluation of a Simple Protein Extraction Method for Species Identification of Clinically Relevant Staphylococci by Matrix-Assisted Laser Desorption Ionization—Time of Flight Mass Spectrometry" (N. Matsuda et al., J. Clin. Microbiology, 50, 3862-3866, 2012), a disruption of the microbes on the sample support plate with 70% formic acid is investigated in addition to the two methods stated, with similarly good results as an external disruption, but requiring significantly less time and work.

In the publication "Evaluation of a Short, On-Plate Formic Acid Extraction Method for Matrix-Assisted Laser Desorption Ionization—Time of Flight Mass Spectrometry-Based Identification of Clinically Relevant Yeast Isolates" (R. L. Gorton et al., J. Clin. Microbiology 52, 1253-1255, 2014) a disruption of cells on the sample support plate is likewise investigated, but these were yeast cells, and the success of the identification is significantly lower than with an external disruption.

In both these publications, the sample is dried and prepared with matrix solution for the ionization by MALDI directly after the disruption on the sample support. Salts or other soluble impurities in particular are not removed: the biological cells applied were obviously always sufficiently clean for the MALDI preparation.

There is therefore still a need for a method which allows cells contaminated with salts and other soluble impurities on a mass spectrometric sample support, for example after incubation in a nutrient droplet on the sample support itself, to be prepared in such a way that the sensitivity of the desorbing ionization (with the aid of MALDI, for example) is virtually fully retained.

SUMMARY OF THE INVENTION

The invention now proposes that the biological cells on the sample spot of a mass spectrometric sample support be disrupted not by adding a matrix solution but in a separate treatment step using matrix-free (organic) acids and/or solvents. The cell proteins released by this disruption adhere surprisingly well to the surface of the sample support and can be washed with washing buffer, for example pure water, to remove salts, detergents, buffer materials and other soluble impurities which can stem from earlier treatment steps.

According to a first aspect, the invention relates to a method for the preparation of proteins from samples of unpurified biological cells (e.g., microorganisms) on a sample support for the mass spectrometric determination of cellular properties, for example the taxonomic classification of microorganisms or their resistance to an antimicrobial substance, comprising the steps:

Provide the biological cells on a sample spot of the sample support, which can comprise a stainless steel plate, a plate with hydrophilic anchors in a hydrophobic environment ("AnchorChip™"), or a plate of coated ceramic material, Disrupt the cells with the aid of (organic) acids and/or solvents on the sample spot such that the cell proteins separate from complexes, migrate out of the disrupted cells and are adhesively bonded to the sample spot, Wash the cell proteins on the sample spot with (static) buffer solution, for example by applying a few microliters of an aqueous solution (especially pure deionized water) to the sample spot, leaving it there for a predetermined period of time and then removing it, and Prepare the washed cell proteins for a subsequent desorbing ionization, for example by adding and crystallizing out matrix solution on the sample spot for a subsequent ionization by matrix-assisted laser desorption.

In a variety of embodiments, the provision of the biological cells can comprise the cultivation of the microorganisms in nutrient liquid on the sample spot of the mass spectrometric sample support. Alternatively, the microorganisms can also be cultivated in an external culture vessel with subsequent transfer of the (unpurified) cultivated microorganisms onto the sample spot of the sample support.

If the biological cells contain microorganisms, these can be cultured on different sample spots of the sample support in nutrient liquid with and without the addition of an antimicrobial substance, and their resistance to the antimicrobial substance can then be determined by further growth in the presence of this substance.

In different embodiments, the growth in the presence of the antimicrobial substance can be determined by comparing it with a reference substance added in a dosed quantity, see in particular EP 2 806 275 B1 and WO 201 4/1 8751 7 A1, whose entire content is to be incorporated in the present disclosure by reference.

The cellular properties, particularly of microorganisms, are preferably determined on the basis of mass spectrometric protein signals in the mass range above m/z 3,000, in particular between around m/z 3,000 and m/z 15,000.

A preferred variant of a method for determining resistances to antibiotics/antimycotics in accordance with principles of the invention can comprise the following steps, for example:

(1) Apply cells in culture media with and without antibiotics/antimycotics to different sample spots of the sample support, (2) Incubate in a chamber for a time depending on the species and the antibiotics, said chamber providing constant conditions (particularly humidity and temperature), (3) Dry the samples on the sample spots at a higher temperature, (4) Add 1 microliter of 70% formic acid in water in order to disrupt the cells and allow the proteins to diffuse out, (5) Dry the disrupted cells on the sample spots at a higher temperature, (6) Add 3 microliters $H_2O$ to the sample spots, let it react for a short time (~3 minutes) and draw it off (either with a pipette or with a special device for removing liquids from the sample spots), (7) Allow the remaining moisture to dry on the sample spots, (8) Pipette matrix solution (where appropriate with an internal standard) onto the sample spots and allow to dry, (9) Measure the protein profiles with a mass spectrometer, for example a MALDI time-of-flight mass spectrometer.

In step (3), the temperature can be between 30° and 60° Celsius, for example, or in rare cases even higher. In step (4), other denaturing volatile solvents can also be used, e.g. 50% acetone in water or 50% acetonitrile, 2.5% trifluoroacetic acid and 47.5% water in water.

Although the method proposed here, whereby the washing procedure takes place on the sample support itself, takes a few minutes longer than a method without washing, it has significant advantages. Surprisingly, the heavy proteins released from the cell remain bonded relatively firmly to the surface of the sample support during the washing step, and are therefore largely insoluble; only the salts and other soluble constituents, for example from the culture medium, go into solution and are removed together with the washing buffer. Surprisingly, this works both on sample support plates made of polished stainless steel and on the familiar anchor targets ("AnchorChip™") and on the "biotargets", made of ceramic material, which have recently come onto the market. If, in contrast, one followed the procedure of drawing off the culture supernatant from a sample spot instead of allowing it to dry, as described in the patent application PCT/DE2016/100561 as the preferred method, there would be a danger of losing microbial species which have little or no adhesion to the sample support surface. Some salmonella species can be given as examples here; they are flagellates and thus swim on the surface of the liquid and could therefore be easily drawn off.

Comparative measurements show that the spectra obtained with the aid of washing on the sample support are of considerably better quality than spectra of unwashed samples because the quantity of salts which interfere with the ionization (particularly with the MALDI method) is greatly reduced by the washing step.

According to a further aspect, the invention relates in particular to a method for the preparation of proteins from samples of biological cells (e.g. microorganisms) for the mass spectrometric determination of cellular properties, for example the taxonomic classification or the resistance of microorganisms to an antimicrobial substance, comprising the steps:

Culture the biological cells in nutrient liquid directly on a sample spot of a mass spectrometric sample support, which can comprise a stainless steel plate, a plate with hydrophilic anchors in a hydrophobic environment ("AnchorChip™"), or a plate made of coated ceramic material, Disrupt the cultured cells on the sample spot with the aid of (organic) acids and/or solvents such that the cell proteins separate from complexes, migrate out of the disrupted cells and are adhesively bonded to the sample spot, Wash the cell proteins on the sample spot with a (static) buffer solution, for example by applying several microliters of an aqueous solution (especially pure deionized water) to the sample spot, leaving it there for a predetermined period of time and then removing it, and Prepare the washed cell proteins on the sample spot for a subsequent desorbing ionization, for example by adding and crystallizing out matrix solution on the sample spot for a subsequent ionization by matrix-assisted laser desorption.

Deionized water, pure or slightly acidified, in particular has proved to be suitable as a washing buffer for the methods described in this disclosure.

DETAILED DESCRIPTION

Figure 1:
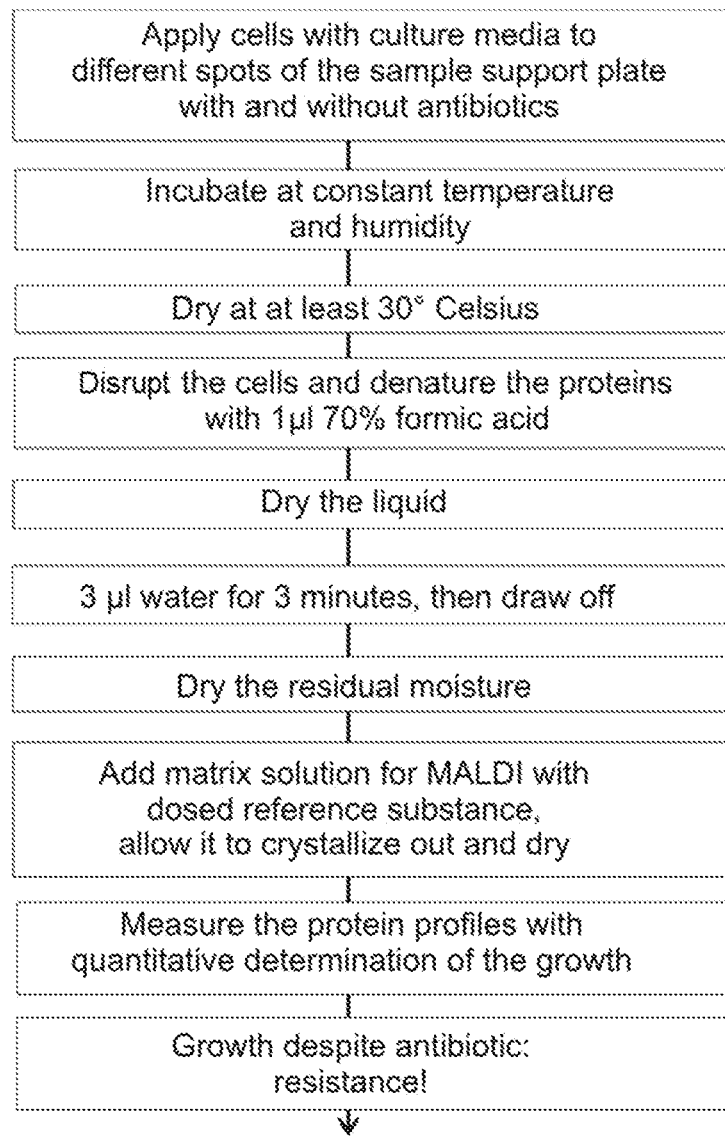
FIG. 1 shows the steps of a method used to determine the resistance of microorganisms.

The invention proposes that the cells on the mass spectrometric sample support are not disrupted by adding matrix solution for a subsequent ionization by matrix-assisted laser desorption (MALDI), but that they are disrupted in a separate treatment step using (organic) acids and/or solvents. Surprisingly, the heavy proteins released from the cells then adhere to the sample support, and so they can be washed there directly with buffer solution to remove salts and other soluble impurities, without significant quantities of proteins being lost to the analysis through being washed out.

Cells of biological materials such as microorganisms or tissue cells which have been applied to sample support plates are usually disrupted by adding a solution which comprises matrix substance for a subsequent ionization by matrix-assisted laser desorption (MALDI) and an organic solvent. The matrix substances are essentially organic acids, which in conjunction with the organic solvent destroy the cell walls, break up the protein complexes, for example the ribosomes, inside the cells and allow the proteins to migrate out of the cell. The ribosomal proteins are particularly suitable for the taxonomic identification of microorganisms. The matrix material crystallizes out when the samples are dried, and the proteins are embedded in the crystals. They can then be vaporized in the mass spectrometer by laser bombardment and ionized by protonation. But if nutrient liquid or some of the disruption liquid is still adhering to the cells, the protonation process is severely impaired by salts, other buffer materials, detergents and other soluble impurities of these liquids. The cells themselves can also contain salts released by the disruption, which possibly interfere with the process of ionization.

Since salts and other impurities in the samples on the sample support plates have a very detrimental effect particularly on a subsequent ionization by matrix-assisted laser desorption (MALDI), the invention proposes that the cells present on the mass spectrometric sample supports should not be disrupted by simply adding a matrix solution, but that the cells should first be disrupted in a separate treatment step using (organic) acids and/or solvents without matrix substances. Although proteins actually display only low adhesion to metal surfaces, intriguingly the proteins released by this disruption adhere quite well to the surface of the usual sample supports and can be washed carefully with buffer solution (for example aqueous solution) to remove salts in particular. Surprisingly, this works both on sample support plates made of polished stainless steel and on the familiar, commercially available anchor plates ("AnchorChip™"), which contain hydrophilic sample "spots" in a hydrophobic environment, and for the "biotargets", made of coated ceramic material, which have recently come onto the market. It appears that the proteins from the cells are denatured to such an extent by the disruption fluids that they have sufficient reactive adhesion sites by which they adhere to the surface.

The washing of disrupt peptides which are adhesively bonded to surfaces is already known, but usually on surfaces prepared in a very particular way. The paper "Paraffin-wax-coated plates as matrix-assisted laser desorption/ionization sample support for high-throughput identification of proteins by peptide mass fingerprinting" (N. S. Tannu et al., Analytical Biochemistry 327 (2004) 222-232) compares the washing of peptides obtained by tryptic digestion of proteins in ZipTip$_{C18}$ pipette tips with the washing on different types of sample support surfaces. The washing on anchor plates is reported to be practicable, although plates with coatings of paraffin wax are supposed to give even better results. It should be noted here that the analytes of interest in the paper by N. S. Tannu et al. are trypsin-digested, and thus very severely denatured peptides essentially in the mass range below m/z 3,000 Daltons, whereas the present invention targets undigested cell proteins in the mass range of around 3,000 to 20,000 Daltons from disrupted biological cells as analytes of interest, whose adhesion behavior cannot be compared to that of digestion products. The prevailing opinion to date has been that intact proteins which have not been denatured exhibit only slight adhesion to foreign surfaces; the realization that the heavy proteins from the cell disrupts actually adhere relatively firmly to the sample support plates was therefore completely unexpected.

In the paper "Non-specific, on-probe cleanup methods for MALDI-MS samples" (Y. Xu et al., Mass-Spectrometric Reviews, 2003, 22, 429-440), sample support plates are coated with films of commercial polymers, thin layers of matrix material, self-ordering monomolecular layers and ultrathin polymer layers, and are investigated as to their suitability for washing proteins adsorbed on them. For some of the surfaces, it was possible to detect that the proteins formed hydrogen bonds which allowed the washing. No uncoated sample support plates were investigated.

Furthermore, the paper "Compressed matrix thin film (CMTF)-assisted laser desorption ionization mass spectrometric analysis" (L. Huang et al., Analytica Chimica Acta 786 (2013) 85-94) describes the washing of proteins which are adhesively bonded to a thin-layer film of the matrix substance which has been compressed for this purpose. Interestingly, experiments done by the applicant with washing on thin matrix layers showed that a subsequent additional application of matrix solution was absolutely imperative to obtain meaningful mass spectra, albeit it that the mass spectra were only low quality.

The disclosure WO 2004/072616 (PCT/US2004/003890; J. W. Finch and J. C. Gebler; "A SAMPLE PREPARATION PLATE FOR MASS SPECTROMETRY") also mentions a washing of immobilized proteins but on a special preparation plate with wells to hold the samples, which is unsuitable for use as a sample support in mass spectrometry, and not on a mass spectrometric sample support as is used to insert specially prepared samples for a desorbing ionization into an ion source.

A first, particularly preferred embodiment of a method in accordance with principles of the invention which determines resistances of microorganisms can, for example, comprise the steps shown in FIG. 1:

(1) The cells are applied to different sample spots of a sample support plate together with culture media (nutrient solution) with and without different antibiotics/antimycotics in one or various concentrations,
(2) this is followed by an incubation for a specified time in a chamber which provides constant conditions for humidity and temperature in particular, where the time can depend on the species and the antibiotics,
(3) the samples are dried on the sample spots at temperatures between 30° and 60° Celsius,
(4) 1 microliter of a solution of 70% formic acid in water is added to disrupt the cells and denature the cell proteins,
(5) the sample spots are allowed to dry at a higher temperature,
(6) 3 microliters of water are added to the sample spots, allowed to act for a short time (around 3 minutes) and drawn off either with a pipette or a special device for removing liquids from the sample spots,
(7) the remaining moisture on the sample spots is allowed to dry,
(8) matrix solution (where appropriate with an internal standard) is pipetted onto the sample spots and allowed to dry,
(9) the protein profiles are measured with a mass spectrometer, in particular a MALDI time-of-flight mass spectrometer,
(10) if growth occurs despite an antibiotic of a specific concentration, a resistance to this antibiotic exists at this concentration; growth in nutrient solutions using different concentrations of the antibiotic allows the minimum inhibitory concentration to be determined.

In this example, the washing procedure using deionized pure water consists in dissolving the water-soluble constituents in water at rest and removing these constituents that are detrimental to the ionization process by removing the water. The washing procedure can be repeated, if required. More vigorous washing in moving water should be avoided, since it can lead to losses in the case of some cellular proteins.

Figure 2:
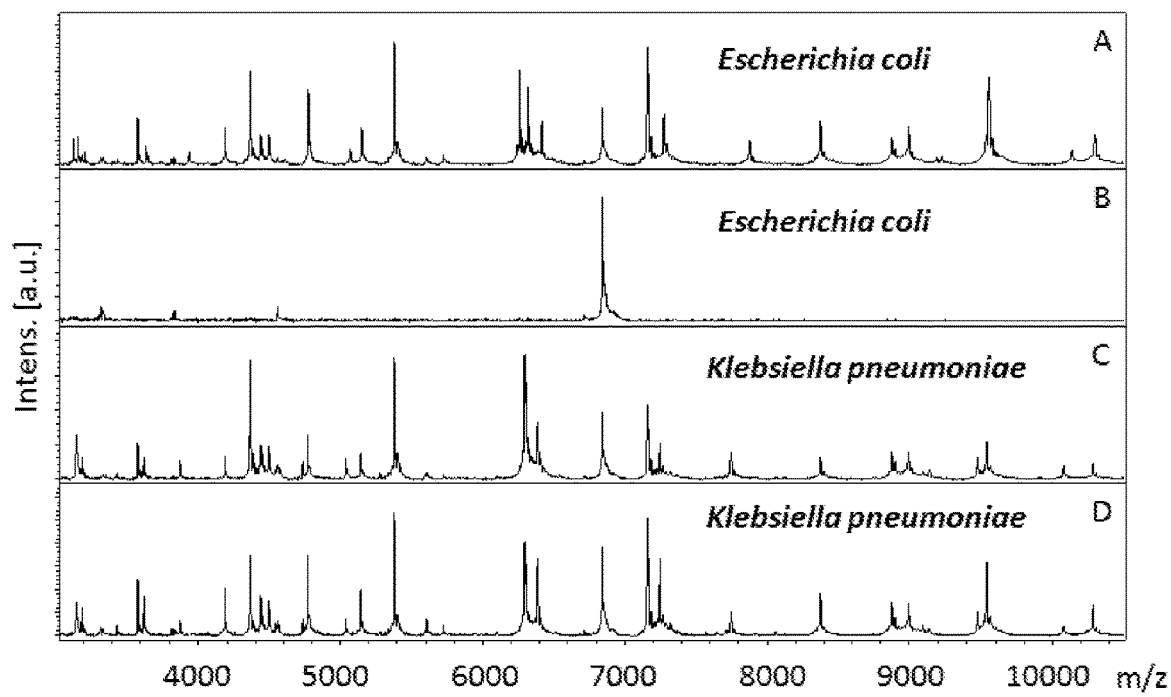
FIG. 2 illustrates mass spectra acquired after a procedure as outlined in FIG. 1 had been conducted. These mass spectra are of an antibiotic-sensitive bacteria strain (*E. coli*.) and an antibiotic-resistant bacteria strain (*Klebsiella pneumoniae*) after being cultured in the absence and in the presence of an antibiotic respectively. Spectrum B shows only the signal of a reference substance.

FIG. 2 shows mass spectra of an antibiotic-sensitive bacterial strain (*E. coli.*) and an antibiotic-resistant bacterial strain (*Klebsiella pneumoniae*), which were each cultured once with and once without the addition of an antibiotic and prepared according to a procedure from FIG. 1. The individual graphs illustrate from top to bottom:

A: Sensitive strain *E. coli.* in Mueller-Hinton medium (a culture medium) without antibiotic;
B: Sensitive strain *E. coli.* in Mueller-Hinton medium with antibiotic (only mass signals of the reference substance added in a dosed quantity stand out here);
C: Meropenem-resistant strain *Klebsiella pneumoniae* in Mueller-Hinton medium without antibiotic; and
D: Meropenem-resistant strain *Klebsiella pneumoniae* in Mueller-Hinton-medium with antibiotic.

From the distinct protein mass signals in the mass range above m/z 3,000 in all spectra in which growth is detected, it is evident that the washing step on the sample support itself after disruption does not significantly deplete the quantity of disrupted proteins of the bacteria from the sample support. The method is therefore very well suited to the preparation of biological cell samples on the sample support itself for subsequent desorbing ionization and mass spectrometric analysis, for example to determine the resistance as a cellular property.

Abnormal eukaryotic cells, for example cancer cells, can similarly be tested for resistance to drugs. Unicellular fungi, likewise eukaryotic, can be identified just like other microorganisms, at least to the taxonomic level of the species, and can be tested for resistances to antibiotics (here: antimycotics). Mycelium-forming fungi can also be examined mass spectrometrically, however. The patent specification U.S. Pat. No. 8,980,577 B2 (T. Mayer, 2012) provides a method for the taxonomic classification of mycelium-forming fungi which consists in cultivating fresh hyphae with considerable agitation to avoid adherence to surfaces. Each time they adhere to a surface, a metabolic restructuring takes place which changes the mass spectra. By comparing these with reference spectra, it is thus possible to arrive at unequivocal identifications. Processing these mycelium-forming fungi from the liquid culture involves various time-consuming steps, such as centrifugation. According to the method described here, the fungi can be applied directly from the liquid culture to the sample spots of the sample support plate and prepared for the mass spectrometric identification. To test for resistances to antimycotics, the fungal cells can, in contrast, be cultured on the sample spots of the sample support plates in culture media with and without antimycotics. The metabolic restructuring is not important when determining growth in the presence of antimycotics.

Figure 4:
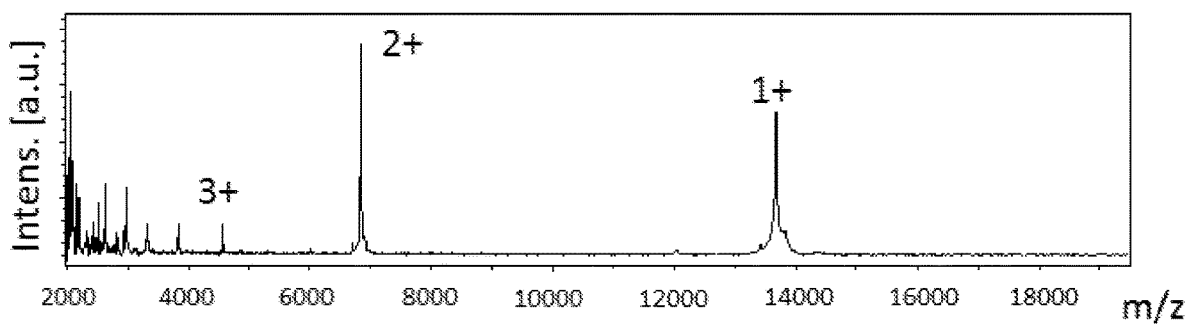
FIG. 4 shows a mass spectrum of the pure nutrient liquid, which was treated and washed according to the procedure of the invention using the washing of the adhesively bonded cell proteins in accordance with FIG. 1. Although the nutrient liquid contains peptides, the mass spectrum is clean, and above 4,000 atomic mass units (Daltons) it contains only the signals of the singly charged (1+), doubly charged (2+) and triply charged ions (3+) of the reference substance added in a dosed quantity.

The nutrient solution for the cultivation of the biological cells on the sample support generally consists of a meat extract and hydrolyzed casein, i.e. it contains proteins and peptides. The nutrient solution, which is not removed but only dried and washed, could thus generate interfering mass signals of the proteins and peptides in the mass spectrum of the cells. This is surprisingly not the case, however, as the mass spectrum in FIG. 4 shows. There are no interfering mass signals at all apart from the mass signals (1+), (2+) and (3+) of the reference substance in the mass range used between m/z 4,000 and 18,000 Daltons. This means that the peptides from the nutrient solution are either so small that they do not interfere, or that they remain soluble and are removed in the washing step.

Although the method proposed here, whereby the washing procedure takes place on the sample support itself, takes a few minutes longer than a method without washing, it has significant advantages. Surprisingly, the proteins released from the cell remain relatively firmly bonded to the hydrophilic surface of the sample support during the washing step, and are therefore largely insoluble; only the salts and other soluble constituents, for example from the culture medium, go into solution and are removed together with the washing buffer. Surprisingly, this works both on sample support plates made of polished stainless steel and on the familiar anchor targets ("AnchorChip™") and on the "biotargets", made of ceramic material, which have recently come onto the market. If, in contrast, one followed the procedure of drawing off the culture supernatant from a sample spot, as described in the patent application PCT/DE2016/100561 as the preferred method, there would be a danger of losing microbial species which have little or no adhesion to the sample support surface. Some salmonella species can be given as examples here; they are flagellates and thus swim on the surface of the liquid and could therefore be easily drawn off.

As comparative measurements show, the spectra from the method comprising a washing step on the sample support surface itself are of considerably better quality (better signal-to-noise ratio) than spectra of unwashed samples because the quantity of salts, which interfere with the ionization (particularly with the MALDI method), is significantly reduced by the washing step.

The above-described special embodiment of the method can be modified in a wide variety of ways. For example, other denaturing, volatile solvents for the disruption of the cells can be used in step (4), e.g. 50% acetone in water or 70% formic acid in water. It is possible to use sample support plates whose sample spots are pre-coated with active substances, for example by applying different types of antibiotic/antimycotic or the same antibiotic/antimycotic in graduated quantities (to determine the minimum inhibitory concentration, for example). The sample spots can also contain pre-dosed quantities of insoluble reference substances for quantitative estimates. The reference substances should be able to dissolve in the matrix solution, but not in the buffer solution of the washing step.

Figure 3:
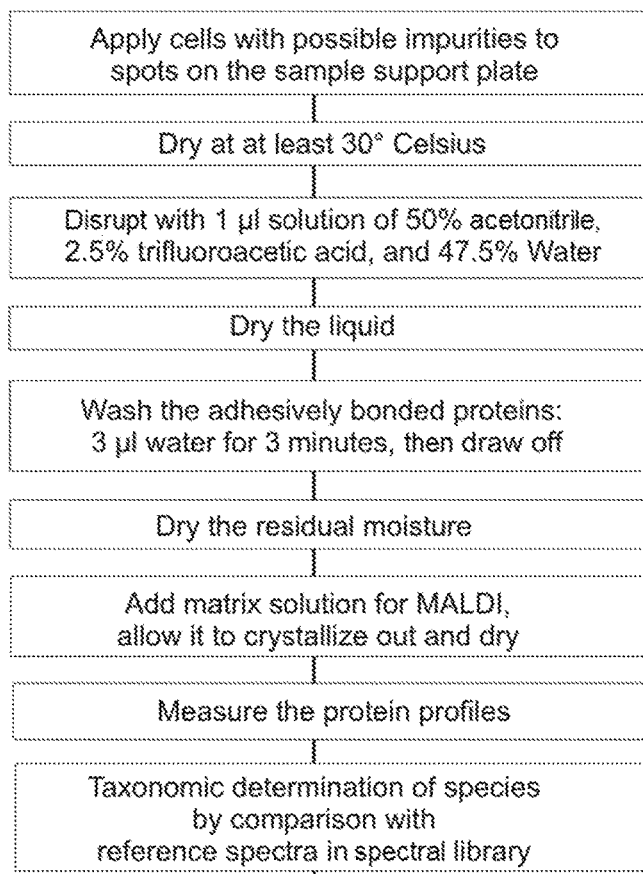
FIG. 3 depicts a simple method for the taxonomic identification of contaminated microorganisms which uses a washing step according to principles of the invention.

A different embodiment of the method according to principles of the invention is illustrated in FIG. 3 and relates to microorganisms and other cells which are not cultivated on the sample support plate, but are simply applied to the sample support for the purpose of mass spectrometric identification (taxonomic classification), although the sample contains impurities such as salts, detergents and others. The impurities can adhere to the microorganisms of an agar colony, for example. With the automated transfer of microorganisms from colonies on agar dishes, it is often the case that small quantities of the agar, including nutrient liquid, are transferred also. Some types of microorganism may also contain harmful salts within them. These samples can also be disrupted in a separate treatment step without matrix material, as is the case in the method described above. Their denatured proteins can then likewise be subjected to a washing step on the sample support itself.

The desorbing ionization can particularly be an ionization by matrix-assisted laser desorption, where the preparation for the ionization then comprises the addition and crystallizing out of matrix solution. The sample support plate can be made of stainless steel, a plate with hydrophilic anchors in a hydrophobic environment ("AnchorChip™"), or a plate made of coated ceramic material.

The cells can be microorganisms. The property of the microorganisms to be determined can be their resistance or susceptibility to antibiotics/antimycotics. The microorganisms can be cultivated on different spots of the sample support plate in nutrient liquid with and without the addition of antibiotics/antimycotics, and the resistance to an antibiotic/antimycotic can be determined by the further growth in the presence of this antibiotic/antimycotic. Growth in the presence of an antibiotic/antimycotic can particularly be determined by comparison with a reference substances added in a dosed quantity.

In general, biological cells can be analyzed as to their response to chemicals while being cultivated on the sample support in the presence of these chemicals. The reaction of cancer cells to different medical active substances or combinations of active substances can be stated here as an example.

The invention claimed is:

1. A method for the preparation of proteins from samples of biological cells for the mass spectrometric determination of cellular properties, comprising the steps:
    cultivating the biological cells in nutrient liquid directly on a sample spot of a mass spectrometric sample support,
    disrupting the cultivated cells on the sample spot using solvents and/or organic acids, whereby cell proteins separate from complexes, migrate out of the disrupted cells and are adhesively bonded to the sample spot,
    washing the cell proteins on the sample spot with buffer solution, and
    preparing the washed cell proteins on the sample spot for a subsequent desorbing ionization.

2. The method according to claim 1, wherein the washing step is conducted with a static buffer solution.

3. The method according to claim 2, wherein, for the washing step, several microliters of an aqueous solution are applied to the sample spot, remain there for a predetermined period of time and are then removed.

4. The method according to claim 1, wherein the preparation for the desorbing ionization comprises the addition and crystallization of matrix solution on the sample spot for a subsequent ionization by matrix-assisted laser desorption.

5. The method according to claim 1, wherein the mass spectrometric sample support comprises a stainless steel plate, a plate with hydrophilic anchors in a hydrophobic environment, or a plate made of coated ceramic material.

6. The method according to claim 1, wherein the biological cells comprise prokaryotic microorganisms, eukaryotic microorganisms or eukaryotic cells from tissues.

7. The method according to claim 6, wherein one of said cellular properties of the biological cells to be determined is their taxonomic classification, resistance to an antimicrobial substance, or response to drugs or other active substances.

8. The method according to claim 7, wherein the antimicrobial substance is an antibiotic or antimycotic.

9. The method according to claim 7, wherein the biological cells are cultivated on different sample spots of the sample support in nutrient liquid with and without the addition of an antimicrobial substance, and their resistance to the antimicrobial substance is determined by determining a difference in growth between a first cultivation in the presence of the antimicrobial substance and a second cultivation in the absence of the antimicrobial substance, by comparing mass spectrometric signals of the cell proteins from the first cultivation and mass spectrometric signals of the cell proteins from the second cultivation.

10. The method according to claim 7, wherein the biological cells are cultivated on different sample spots of the sample support in nutrient liquid with and without the addition of an antimicrobial substance, and their resistance to the antimicrobial substance is determined by further growth in the presence of the antimicrobial substance, which further growth is determined by comparing mass spectrometric signals of the cell proteins with mass spectrometric signals of a reference substance added in a dosed quantity.

11. The method according to claim 7, wherein a minimum inhibitory concentration of the antimicrobial substance is determined for the biological cells.

12. The method according to claim 1, wherein cultivating the biological cells comprises cultivating the biological cells in the presence of chemicals, and wherein the biological cells are mass spectrometrically investigated as to their response to the chemicals.

13. The method according to claim 1, wherein the cellular properties are determined on the basis of mass spectrometric protein signals in a mass range above m/z 3,000.

14. The method according to claim 13, wherein said mass range extends between m/z 3,000 and m/z 15,000.

15. The method according to claim 1, wherein the solvents and organic acids used for disrupting the cells are matrix-free.

16. The method according to claim 1, wherein the cultivated biological cells are unpurified.

17. The method according to claim 1, wherein the buffer solution comprises pure deionized or acidified water.

18. The method according to claim 1, wherein cultivating the biological cells comprises incubating the mass spectrometric sample support in a chamber which provides constant conditions.

19. The method according to claim 1, wherein soluble impurities are removed by said washing.

20. The method according to claim 19, wherein the soluble impurities encompass salts, detergents, and buffer materials.

21. The method according to claim 1, wherein the nutrient liquid used for cultivating the biological cells comprises meat extract and hydrolyzed casein.

* * * * *